United States Patent [19]

Davis et al.

[11] 4,046,656
[45] Sept. 6, 1977

[54] PHOTOCHLORINATION PROCESS FOR METHYL AROMATIC COMPOUNDS

[75] Inventors: Ralph A. Davis; R. Garth Pews, both of Midland, Mich.

[73] Assignee: The Dow Chemical Company, Midland, Mich.

[21] Appl. No.: 747,859

[22] Filed: Dec. 6, 1976

[51] Int. Cl.² ............................................... B01J 1/10
[52] U.S. Cl. .......................... 204/158 HA; 204/163 R
[58] Field of Search ..................... 204/158 HA, 163 R

[56] References Cited

U.S. PATENT DOCUMENTS

| 2,607,802 | 8/1952 | Britton et al. ............... 204/158 HA |
| 3,816,287 | 6/1974 | Bockman et al. ............... 204/163 R |

*Primary Examiner*—Howard S. Williams
*Attorney, Agent, or Firm*—James B. Guffey

[57] ABSTRACT

The rate of photochlorination of methyl aromatic compounds, such as toluene, cresol, xylene, toluenesulfonyl chloride, methylnaphthalene, diphenylmethane, etc., is increased when carried out in the presence of bromine.

15 Claims, No Drawings

PHOTOCHLORINATION PROCESS FOR METHYL AROMATIC COMPOUNDS

BACKGROUND OF THE INVENTION

This invention relates to photochlorination of methyl aromatic compounds.

Photochlorination of methyl aromatic compounds such as toluene, o- or p-toluenesulfonyl chloride, 3-chloro-4-methylbenzenesulfonyl chloride, and o-, m- or p-xylenesulfonyl chlorides, is known. See for example British Pat. No. 956,857; British Pat. No. 1,401,038; U.S. Pat. No. 3,230,268; Miller et al., "The Displacement of Aromatic Substituents by Halogen Atoms", *Journal of the American Chemical Society*, Vol. 79, pp. 4187–4191 (1957); and Miller, "A Regiospecific Synthesis of 4-Chloroalkylbenzenes", *Journal of Organic Chemistry*, Vol. 38, No. 6, pp. 1243–1245 (1973). Although good yields of certain chlorinated products have been reported, the time required to produce chlorinated products, in which the benzylic hydrogens have each been replaced by chlorine, are unduly long.

It would therefore be highly desirable to provide a photochlorination process wherein reasonable yields of methyl aromatic products exhibiting total benzylic hydrogen displacement by chlorine is achieved in reduced reaction times.

SUMMARY OF THE INVENTION

This invention is an improved process for the photochlorination of methyl aromatic compounds. Such process comprises contacting the methyl aromatic compound (hereinafter also referred to as the aromatic reactant) with chlorine in the presence of ultraviolet radiation and an accelerating amount of bromine.

As used herein an "accelerating amount" means an amount of bromine sufficient to measurably increase (preferably by at least about 25 percent, more preferably by at least about 50 percent) the rate of formation of α-chloro-substituted methyl aromatic product.

In such process each benzylic hydrogen of the aromatic reactant is replaced by a chlorine atom, thereby forming the aforementioned α-chloro-substituted aromatic product.

Certain of the products thereby produced are valuable intermediates for the preparation of selective herbicides, such as N,N-dimethyl-N'-(m-trifluoromethylphenyl)urea; N-ethyl-N-(2-methyl-2-propenyl)-2,6-dinitro-4-(trifluoromethyl)-benzenamine; N-(cyclopropylmethyl)-2,6-dinitro-N-propyl-4-(trifluoromethyl)-benzenamine; N',N'-diethyl-2,6-dinitro-4-(trifluoromethyl)-1,3-benzenediamine; N-(2-chloroethyl)2,6-dinitro-N-propyl-4-(trifluoromethyl)-benzenamine; N-butyl-N-ethyl-2,6-dinitro-4-(trifluoromethyl)-benzenamine; 2,6-dinitro-N,N-dipropyl-4-(trifluoromethyl)-benzenamine; and the like.

The presence of bromine in the aforementioned process substantially reduces the reaction time required to obtain the aforementioned α-chloro-substituted methylated aromatic product in reasonable yields (e.g., at least about 40 percent, more commonly at least about 90 percent) based upon the methylated aromatic reactant.

DETAILED DESCRIPTION OF THE INVENTION

This invention is an improved process for the photochlorination of methyl aromatic reactants to form α-chloro-substituted aromatic products wherein each benzylic hydrogen of the aromatic reactant is replaced by a chlorine atom.

Methyl aromatic reactants for the photochlorination of which the improved process of the invention is useful include those of the formula I or II (preferably I).

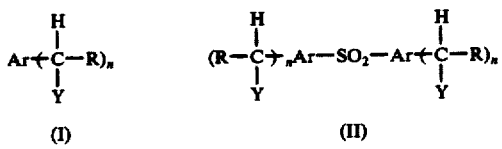

In the methylated aromatic reactant (I) or (II) each Ar is individually an aromatic radical; each R is individually a Y substituent or an aromatic radical, preferably a Y substituent; each Y substituent is individually hydrogen, chlorine or bromine, preferably hydrogen or chlorine, most preferably hydrogen; and each n is individually a positive integer, suitably from 1 to 5, preferably from 1 to 3, more preferably 1 or 2, most preferably 1.

As used herein "aromatic radical" includes radicals such as phenyl, biphenyl, naphthyl, phenoxyphenyl, naphthoxyphenyl, phenylthiophenyl, phenylthionaphthyl, α,α-dichlorobenzylphenyl, α,α-difluorobenzylphenyl and the like, preferably phenyl, biphenyl or naphthyl, most preferably phenyl.

In the aforementioned aromatic reactants the integer, n, cannot exceed the number of ring positions on the aromatic radical, Ar. Further, it is understood that when the integer n is less than the number of available ring positions on the aromatic radical Ar with which such integer is associated, each of the remaining ring positions is individually occupied by an inert substituent or by a chlorine displaceable (i.e., photodisplaceable) substituent.

Similarly in reactants of the formula I or II wherein the radical R is an aromatic radical, each available ring position of such radical is individually occupied by an inert substituent or by a chlorine displaceable substituent.

As used herein the term "inert substituent" means a radical which is not readily displaced from an aromatic nucleus by chlorine under photochlorination conditions. Suitable inert substituents include, for example, hydrogen, fluorine, chlorine, —$CF_3$, —OH, —$OCF_3$, —$OCCl_3$, —$SCF_3$, —$SCCl_3$, —$SO_2CF_3$, —$SO_2CCl_3$, —$COCF_3$, —$COCCl_3$, —$NO_2$, —CN, —$NF_2$ and the like. Preferred inert substituents include hydrogen, fluorine, chlorine, —$CF_3$, —OH, —$OCF_3$, —$OCCl_3$, —$NO_2$ and —CN. The most preferred inert substituents are hydrogen, fluorine and chlorine, especially hydrogen and chlorine.

As used herein a "chlorine displaceable substituent" is a radical which is displaced from an aromatic ring by chlorine under photochlorination conditions. Examples of such chlorine displaceable substituents include bromine, —$SO_2Cl$, —$SO_2Br$, —$SO_2CH_3$, and —$COCH_3$. Preferred chlorine displaceable substituents are bromine, —$SO_2CL$ and —$SO_2Br$, especially —$SO_2Cl$.

In the aforementioned reactants the relative ring positions of the —CHRY groups and any inert or photodisplaceable substituents among themselves (e.g., —CHRY relative to —CHRY) and between each other (e.g., —CHRY group relative to an inert or photodisplaceable substituent) are not critical. Thus, for example, a —CHRY radical can be ortho, meta or para to another such radical or to another ring substituent and other ring substituents can be ortho, meta or para to each other.

Examples of methyl aromatic reactants of the formula I include methyl benzenes such as toluenes (e.g., toluene, α-chlorotoluene, p-chloro-α,α-dibromotoluene, m-bromotoluene, methyl p-tolyl sulfone, methyl m-tolyl ketone, p-toluenesulfonyl chloride, p-cresol, 3,5-dinitrotoluene, 3-cyano-5-(trifluoromethoxy)toluene, diphenylmethane, etc.), xylenes (e.g., o-xylene, α,α'-dichloro-m-xylene, α,α-dibromo-p-xylene, 1,3-dimethyl-5-nitro-benzene, etc.), trimethyl benzenes (e.g., 1,3,5-trimethylbenzene, 5-bromomethyl-1,3-dimethylbenzene, 1,3,5-tris(chloromethyl)benzene, etc.); methyl naphthalenes such as 2-methylnaphthalene, 1-(bromomethyl)-3-cyano-naphthalene, 4-bromo-2-methylnaphthalene, 4-methyl-1-naphthalenesulfonyl bromide, etc.; methyl biphenyls such as p-phenyltoluene, m-(4-bromophenyl)toluene, etc.; methyl diphenyloxides such as p-(phenoxy)toluene, α-bromo-meta-(phenoxy)toluene, etc.; methyl diphenyl sulfides such as p-(phenylthio)toluene, 1,3-dimethyl-5-(phenylthio)benzene, etc.; and the similar methyl aromatic reactants.

The methyl aromatic reactants of the formula II include methylaryl methylaryl sulfones such as bis(p-tolyl)sulfone, bis(4-methyl-2-naphthyl)sulfone, bis(4-methyl-3,5-dinitro-phenyl)sulfone and the like.

Especially preferred methyl aromatic reactants are those wherein each Ar is phenyl or substituted phenyl and each R is a Y substituent. Such reactants thus have the formula III or IV (preferably III)

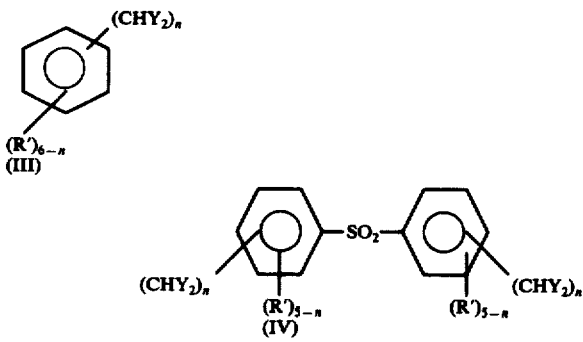

wherein Y and n are as hereinbefore defined and R' is an inert or chlorine displaceable substituent as hereinbefore defined.

Examples of the methyl aromatic reactants of the formula III include toluene, cresol, xylene, α-bromotoluene, 4-nitrotoluene, 4-bromotoluene, 3,5-dinitrotoluene, α-chloro-3-cyanotoluene, α,α-dichlorotoluene, p-toluenesulfonyl bromide, 2-chloro-p-toluenesulfonyl chloride, p-((trichloromethyl)thio)toluene, m-(trichloromethoxy)toluene, p-(trifluoromethoxy)toluene, o-((trifluoromethyl)thio)toluene, p-tolyl trifluoromethyl sulfone, m-tolyl trifluoromethyl ketone, m-tolyl trichloromethyl sulfone, p-tolyl trichloromethyl ketone, methyl p-tolyl sulfone, methyl p-tolyl ketone, and the like.

The methyl aromatic reactants of the formula IV include tolyl tolyl sulfones such as bis(p-tolyl) sulfone, m-tolyl p-tolyl sulfone, bis(3-bromo-4-tolyl) sulfone, bis(2,6-dinitro-4-tolyl) sulfone, bis(3,5-dimethylphenyl) sulfone, and the like.

The sulfone linkage (i.e., the radical —SO₂—) of the reactants of the formulas II and IV is displaced by chlorine under photochlorination conditions thereby forming two ring chlorinated aromatic moieties. Thus, such reactants are not generally desirable for the preparation of chloro-substituted aromatic products wherein ring chlorination is not desired.

Further, since each mole of reactant of the formula II or IV provides two moles of chloro-substituted aromatic product and since a single product is generally desired rather than a product mixture, the two reactant moieties (i.e., (CHRY)̵Ar- or (CHY₂)̵φ—) are preferably selected such that the photochlorinated product of the two moieties will be the same. Most preferably both reactant moieties in such methyl aromatic reactants are themselves the same (i.e., the identity and ring positions of the CHRY— or CHY₂ groups and the remaining substituents on both such moieties are identical).

Bromine is employed as an accelerator in the practice of the invention. The source of bromine can be elemental bromine or a brominated organic or inorganic compound which releases bromine under photochlorination conditions. Suitable brominated organic compounds include, for example, carbon tetrabromide, bromoform, dibromodichloromethane, bromobenzene, etc. Suitable inorganic bromine compounds include for example, hydrogen bromide; alkali metal bromides (e.g., lithium bromide, sodium bromide, potassium bromide, etc.); alkaline earth metal bromides (e.g., magnesium bromide, calcium bromide, etc.); and the like.

When solvent (discussed hereinafter) is employed which contains bromine substituents (e.g., bromobenzene) or when the aromatic reactant (e.g., p-bromotoluene) contains bromine substituents, which bromine substituents are displaced by chlorine under photochlorination conditions, it is generally unnecessary to charge additional bromine (elemental or in the form of a brominated organic or inorganic compound) to the photochlorination process.

Elemental bromine is the preferred bromine source.

When the bromine source is added separately (i.e., as elemental bromine or as a brominated compound which is different from the solvent or the aromatic reactant), it can enter the process in a variety of ways and at various times, so long as a sufficient amount is present for a sufficient time to satisfy the hereinafter presented definition of an "accelerating amount".

For example, the bromine source can be charged initially in conjunction with (e.g., premixed with) solvent, the methyl aromatic reactant or the chlorine feed. It can also be charged individually at the start of the reaction, either as a separate and distinct one shot addition to the reaction vessel or as a separate and distinct continuous feed stream. In addition, it can be added at an appropriate time (or at appropriate times in the case of multiple additions) during the course of the photochlorination after the reaction has been initiated and carried forward for a time in the absence of bromine.

One preferred embodiment of the invention comprises a staged batch process, wherein photochlorination of the methyl aromatic reactant is conducted in the initial stage in the absence of bromine until the rate of reaction measurably decreases. Then bromine is added to the reaction mixture and photochlorination is continued. In such embodiment, one or more subsequent additional photochlorination stages which are carried out in the presence of bromine can optionally be employed.

The amount of bromine employed is not particularly critical to the practice of the invention so long as at least an accelerating amount is employed and so long as more chlorine than bromine is employed. As used herein "an accelerating amount" means an amount of bromine sufficient to measurably increase (preferably by about 25 percent, more preferably by about 50 percent) the rate of formation of the objective α-chloro-substituted methyl aromatic product as compared to the rate of the corresponding reaction in the absence of bromine. Excessive bromine concentration in the reaction mixture can, however, inhibit photochlorination somewhat by virtue of the resulting increased ultraviolet absorption of the reaction mixture. While the balance between reaction rate acceleration and U.V. absorption will vary depending upon such factors as the amount of solvent employed, the intensity of the U.V. source, etc., as a general rule bromine concentrations between about 0.03 and about 3.0, preferably between about 0.05 and about 1.0, more preferably between about 0.05 and about 0.3, most preferably between about 0.1 and 0.15, equivalents of bromine atoms per mole of methyl aromatic reactant are advantageously employed.

With the exception of conducting the reaction in the presence of bromine as hereinbefore described and the increased reaction rates thereby obtained, the practice of the invention is pursuant to conventional photochlorination techniques as hereinafter briefly described.

For example, the chlorination is generally conducted using at least about a stoichiometric amount of chlorine based upon the methyl aromatic reactant employed. Thus, since half the chlorine employed to displace benzylic hydrogen leaves the reaction as HCl, generally at least about one mole of elemental chlorine (or 2 equivalents of chlorine atoms) are employed per equivalent of benzylic hydrogen to be displaced. Naturally additional chlorine can be advantageously employed, as for example when the aromatic reactant contains photodisplaceable nuclear substituents such as those mentioned hereinbefore. Similarly lesser amounts of chlorine can be employed at a corresponding sacrifice in the yield of the objective methyl aromatic reactant (i.e., increased amounts of product wherein less than all of the benzylic hydrogens have been replaced by chlorine).

The photochlorination process of the invention is normally conducted in the liquid phase (generally in a solvent, especially where the methyl aromatic reactant is a solid at the desired reaction temperature) pursuant to conventional photochlorination reaction procedures and conditions. While not critical to the practice of the invention, it is preferable that the process be conducted under essentially anhydrous conditions (e.g., a maximum of about 1000, more preferably about 400, parts per million of water by weight) to avoid hydrolysis of the desired photochlorinated product. Optionally, a free radical generating catalyst, such as azobisisobutyronitrile, azobisisovaleronitrile, etc., can be employed.

The source of ultraviolet radiation can be natural sunlight or an artificial U.V. source can be employed. To divorce the process from uncontrollable meteorological conditions and time of day factors, a conventional artificial source of ultraviolet radiation is preferably employed. Preferably the U.V. source is placed in, or as close as possible to, the vessel in which the process (i.e., reaction) is conducted.

The choice of solvent, if any is used, is not particularly critical to the practice of the invention. However, since the process is generally conducted under reflux conditions, the solvent used is preferably such that the reaction mixture refluxes at the desired temperature and pressure. Furthermore, the solvent employed is advantageously inert to photochlorination; otherwise a portion of the chlorine charged to the process will be nonproductively consumed in chlorinating the solvent.

Thus, the preferred solvents are polychlorinated aliphatic or aromatic hydrocarbon solvents which have suitable boiling points and which are inert to photochlorination. Examples of such solvents include chloroform, carbon tetrachloride, dichlorobenzene, trichlorobenzene, etc., as well as the hereinafter described chloro-substituted methylated aromatic products of the formula V or VI which are liquid at the desired reaction conditions. When a chloro-substituted methyl aromatic product, V or VI, is employed as a solvent, it is naturally preferable that it be identical with the objective chloro-substituted methyl aromatic product being produced via the process of the invention.

The reaction temperature likewise is not particularly critical to the practice of the invention. However, as a general rule, the reaction is advantageously conducted between about 0° C and about 200° C, preferably between about 25° C and about 160° C, more preferably between about 50° C and about 140° C, most preferably between about 60° C and about 120° C.

Control of the reaction temperature is conveniently achieved primarily by controlling the rate at which chlorine is fed to the reaction vessel. However, when the reaction is conducted under reflux conditions, the choice of solvent and the reaction pressure are also important considerations relating to the maximum achievable reaction temperature. Generally, operation with the reaction vessel open to the atmosphere through a reflux condenser and a scrubber is convenient and, therefore, preferred.

The reaction times in absolute terms will depend upon such factors as the reactant involved, the reaction temperature, the rate at which chlorine is fed to the process and the amount of bromine employed. However, as a general rule, the photochlorination will be essentially complete within a period of about 15 hours, often in as little as 3½ hours.

After completion of the reaction, the resulting mixture can be subjected to distillation to remove the solvent (if any and if different from the desired chloro-substituted aromatic product) and to purify the desired product.

Examples of the resulting chloro-substituted aromatic products of the improved process of the invention include those of the general formula

 (V)

(VI)

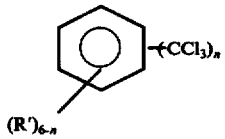

wherein Ar and $n$ are as hereinbefore defined, R is chlorine or an aromatic radical as hereinbefore defined, and R' is an inert substituent as hereinbefore defined.

Naturally the integer $n$ cannot exceed the number of ring positions on the aromatic radical. When $n$ is less than the number of available ring positions on the Ar radical, each of the remaining ring positions is individually occupied by an inert substituent such as those mentioned hereinbefore.

Similarly when the radical R is an aromatic radical, each available ring position of such radical is individually occupied by an inert substituent.

Representative chloro-substituted aromatic products of the formula V include α,α,α-trichlorotoluenes such as (trichloromethyl)benzene, 5-cyano-1,3-bis(trichloromethyl)benzene, 4-fluoro-1-(trichloromethyl)benzene, 4-(trichloromethyl)phenol, 1-(trichloromethyl)-4-(trifluoromethoxy)benzene, 2,4-dichloro-1-(trichloromethyl)benzene, 1,3,5-tris(trichloromethyl)benzene, 3,5-dinitro-1-(trichloromethyl)benzene, etc.; chlorinated diaryl methanes, such as dichlorodiphenylmethane, difluoro-bis(p-(trichloromethyl)phenyl)methane, dichloro-bis(3,5-dinitrophenyl)methane, dichloronaphthyl-phenylmethane, etc.; (trichloromethyl)naphthalenes such as 2-(trichloromethyl)naphthalene, 2,4-bis(trichloromethyl)naphthalene, 4,5-dinitro-2,7-bis(trichloromethyl)naphthalene, etc.; diaryloxides, such as m-phenoxy-(trichloromethyl)benzene, p-(2,4,6-trichlorophenoxy) (trichloromethyl)benzene, etc.; (trichloromethyl)diarylsulfides, such as 6-phenylthio-3-(trichloromethyl)naphthalene, 4-(p-fluorophenylthio)-(trichloromethyl)benzene, etc.; and similar α-chloro-substituted methyl aromatic compounds.

Examples of α-chloro-substituted methyl aromatic products of the formula VI include (trichloromethyl)benzene, 4-chloro-1-(trichloromethyl)benzene, 4-(trichloromethyl)phenol, 2,4-dichloro-(trichloromethyl)benzene, 4-chloro-2,5-difluoro-(trichloromethyl)benzene, 1-(trichloromethyl)-3-(trifluoromethoxy)benzene, 2-chloro-1-(trichloromethyl)-4-(trichloromethyl)thio)benzene, 4-(trichloromethyl)phenyl trifluoromethyl sulfone, 2-cyano-4-(trichloromethyl)phenyl trifluoromethyl ketone, 1,4-bis(trichloromethyl)benzene, 1-(trichloromethyl)-4-(trifluoromethyl)benzene, 4-chloro-1,2-bis(trichloromethyl)benzene, 5-cyano-1,3-bis(trichloromethyl)benzene, 1,2,3-tris(trichloromethyl)benzene, 5-chloro-1,2,4-tris(trichloromethyl)benzene, 4-nitro-1,3,5-tris(trichloromethyl)benzene, 3,5-dinitro-1-(trichloromethyl)benzene, 3,5-bis(trichloromethyl)-1-(trifluoromethyl)benzene, and the like.

More preferred chloro-substituted methyl aromatic products of the formula VI include for example (trichloromethyl)benzene, 4-fluoro-1-(trichloromethyl)benzene, 4-chloro-1-(trichloromethyl)benzene, 3-nitro-1-(trichloromethyl)benzene, 3,5-dinitro-1-(trichloromethyl)benzene, 2,4-dichloro-1-(trichloromethyl)benzene, 3-cyano-4-fluoro-1-(trichloromethyl)benzene, 2,4,5-trichloro-1-(trichloromethyl)benzene, 4-(trichloromethyl)phenol, 2-chloro-4-(trichloromethyl)phenol, (p-(trichloromethyl)phenyl) (trifluoromethyl) ketone, trichloromethyl m-(trichloromethyl)phenyl ketone and the like; especially (trichloromethyl)benzene, 4-chloro-1-(trichloromethyl)benzene, 2,4-dichloro-1-(trichloromethyl)benzene, 3-nitro-1-(trichloromethyl)benzene and 3,5-dinitro-1-(trichloromethyl)benzene.

Most preferred chloro-substituted methyl aromatic products of the formula VI include (trichloromethyl)benzene, 4-chloro-1-(trichloromethyl)benzene, and 2,4-dichloro-1-(trichloromethyl)benzene.

The process of the invention is further illustrated, though not limited by, the following examples.

EXAMPLE 1

Photochlorination of p-Toluenesulfonyl chloride in Presence of $Br_2$

A one-liter 3-neck flask is equipped with a sparge tube, a stirrer and a 16 inch Vigreaux reflux condenser. The condenser outlet is connected to a water scrubber via an ice cooled trap.

A 275 watt sunlamp is used as the source of ultraviolet radiation (i.e., the U.V. source). It is mounted about 6 inches from the one-liter flask.

One mole (191 g) of p-toluenesulfonyl chloride, 300 g of carbon tetrachloride and 10 g of bromine are charged to the flask. The sunlamp is turned on and the chlorine flow is started. Chlorine addition is slow until the reaction is initiated (evidenced by HCl evolution). Then the chlorine is fed, with rapid stirring, as fast as it can be used (about 60 g/hr). The temperature is controlled between about 75 and about 80° C by $CCl_4$ reflux.

As bromine is passed from the reaction vessel (the flask) into the cold trap, it is replaced by adding a 5 g portion of bromine after 1½ hours and another 5 g portion 5 hours after initiation of the reaction.

The reaction proceeds rapidly and is complete at the end of 5¼ hours.

Analyses of the reaction products in the reaction mixture taken at various reaction time intervals via gas-liquid chromatography (GLC) are summarized below.

| Chlorinated Product | Reaction Time | | | |
|---|---|---|---|---|
| | 1½ hrs | 3 hrs | 4 hrs | 5¼ hrs |
| p-$CH_2Cl\phi Cl$ | 2.5% | 1.9% | 0.7% | 0.7% |
| p-$CHCl_2\phi Cl$ | 50.8% | 39.6% | 16.2% | 0.7% |
| p-$CCl_3\phi Cl$ | 45.0% | 57.6% | 81.6% | 97.0% |
| Unknown | 1.7% | 0.9% | 1.5% | 1.6% |

After the $CCl_4$ is stripped off, 222 g (96 percent) of crude product remains which is analyzed to be 97 percent p-$Cl\phi CCl_3$ by GLC. Infra-red (IR) analysis confirms the identity of the product.

Comparative Photochlorination of p-Toluenesulfonyl chloride in the Absence of Bromine To the reactor of Example I, one mole (191 g) of p-toluenesulfonyl chloride and 300 g of $CCl_4$ are charged. The mixture is chlorinated with $Cl_2$ at the maximum chlorine utilization rate under U.V. light at a temperature between about 60° and about 70° C for a total of 6 hours.

Chlorination, after initiation, is rapid at first. At the end of 2 hours, most of the p-toluenesulfonyl chloride has been reacted, but the major product at this point appears to be 4-chloro-α-chlorotoluene.

Continued chlorination for an additional 4 hours (6 hours total) results in the following product mixture as determined by GLC analysis:

p-$CH_2Cl\phi Cl$ — 6 mole percent p-$CHCl_2\phi Cl$ — 66 mole percent p-$CCl_3\phi Cl$ — 28 mole percent At this point the reaction has become so slow that an estimated 30 to 35 hours of additional reaction time is necessary to convert the balance of the product to p-chloro-α,α,α-trichlorotoluene.

Comparison of the product distribution after only 1½ hours in Example I with the product distribution after 6 hours in the comparative experiment reveals that formation of p-$CCl_3\phi Cl$ in the presence of bromine occurs substantially faster than in the absence of bromine. In addition, the lower reaction temperature generated by the reaction in the absence of bromine further evidences the slower reaction rate.

EXAMPLE II

Photochlorination of p-Bromotoluene

To the reactor of Example I are added 95 g (0.55 mole) of p-bromotoluene and 300 g of CCl$_4$.

Chlorine is fed to match the reaction rate. The solution becomes red with bromine almost immediately and the reaction is controlled at a temperature between 70° and 80° C. The reaction is very rapid for about the first hour then it proceeds more slowly. After about 1 hour the majority of the bromine is distilled off with some CCl$_4$. The reaction is continued for another 1¼ hours at a reduced Cl$_2$ feed and lower temperature (60°–70° C).

GLC analysis and IR analysis indicates the following product composition:

p-chloro-α,α,α-trichlorotoluene — 95 percent
p-chloro-α,α-dichlorotoluene — 2 percent
Unknown (perhaps ring dichlorinated) — 3 percent

EXAMPLE III

Photochlorination of 2-Chloro-p-Toluenesulfonyl chloride in the Presence of Bromine A four-liter chlorination reactor equipped with an internal light well is fitted with a gas sparge tube and a ten bulb reflux condenser venting to a scrubber.

The reactor is charged with 2238 g (9.95 moles) 2-chloro-p-toluenesulfonyl chloride and 300 ml of CCl$_4$. A General Electric lamp (H100A4) is used as the light source.

With the light turned on, Cl$_2$ is fed at about 300 grams per hour after the reaction initiated. The temperatures are maintained between 100° and 140° C.

At the end of 5¼ hours the reaction rate has slowed and 10 ml of bromine in 50 ml of CCl$_4$ are added. The chlorination is continued for an additional 5 hours at between 120° and 150° C at a somewhat slower chlorine feed rate (70 to 100 g/hr). An analysis of the product at the end of the additional 5 hour period indicates that it is 63 percent 2,4-dichloro-α,α,α-trichlorotoluene and 37 percent 2,4-dichloro-α,α-dichlorotoluene.

An additional 5 ml of Br$_2$ in 50 ml of CCl$_4$ is added and the chlorination is continued at about 60 g/hr of chlorine feed at between 120° and 154° C for an additional 7 hours.

A total of 2521 g, 35.5 moles of Cl$_2$ has thus been fed in the 17.5 hour period. This gives a Cl$_2$ efficiency of 84 percent. After stripping under vacuum to remove CCl$_4$ a 2556 g portion of product, representing a 98 percent recovery, is isolated. The product is analyzed by GLC, NMR and IR and found to be about 97 percent 2,4-dichloro-α,α,α-trichlorotoluene.

EXAMPLE IV

Photochlorination of p-Chlorotoluene in the Presence of Bromine

To a 1-liter, 3-neck flask, equipped with an 18 inch Vigreaux condenser, a stirrer and a gas sparge tube and connected via a dry ice trap to a scrubber, is charged 253 g (2 moles) of p-chlorotoluene and 300 g of CCl$_4$.

The mixture is partially saturated with Cl$_2$ and then irradiated with a sunlamp. When the reaction is initiated (HCl evolution), Cl$_2$ is fed as rapidly as possible (with continued irradiation) to maintain a slight excess of Cl$_2$ in the solution. The reaction slows after about 1 hour. Irradiation is stopped and the CCl$_4$–Cl$_2$-chlorotoluene solution which has collected in the dry ice trap is recharged to the flask. A 5 ml portion of Br$_2$ is also added to the reaction mixture. The flask is again irradiated and Cl$_2$ is fed as rapidly as it will react. Chlorination is continued for another hour and 15 minutes.

The temperature rises rapidly in the initial stage of the reaction and remains in the 75°–80° C range with a heavy CCl$_4$ reflux. In the latter stage of the reaction, temperatures as high as 95°–100° are reached.

A 454 g portion, (yield 98.5 percent) of product (98+ percent p-ClφCCl$_3$) is recovered by stripping off the carbon tetrachloride.

Comparative Photochlorination of p-Chlorotoluene in Absence of Bromine

To the apparatus of Example IV is added 253 g (2 moles) of p-chlorotoluene and 300 g of CCl$_4$. Chlorine is fed to the reaction as rapidly as possible. The temperature rises to between 90° and 95° C in about 30 minutes and remains there for the duration of the reaction. The product is sampled at various time intervals during the course of the reaction. The product distribution at the various times is as follows:

| Time | 2 hrs 15 mins | 5 hrs 15 mins | 8 hrs 30 mins |
|---|---|---|---|
| para-Cl-φ-CH$_3$ | 6.9% | 0% | 0% |
| para-Cl-φ-CH$_2$Cl | 58.8% | 14.4% | 1.3% |
| para-Cl-φ-CHCl$_2$ | 33.1% | 39.9% | 2.0% |
| para-Cl-φ-CCl$_3$ | 1.2% | 45.7% | 96.7% |

A total of 457 grams (99 percent yield) of product mixture is recovered after the CCl$_4$ is stripped off.

As is apparent from comparing the data for the comparative reaction at 2 hours and 15 minutes with the data from Example IV, formation of the desired product (i.e., p-chloro-α,α,α-trichlorotoluene) is substantially accelerated in the presence of bromine.

Alternatively, comparison of the product distribution at 8½ hours for the comparative experiment with the product distribution at 2¼ hours (i.e., at the completion of the reaction) in Example IV reveals that the reaction time required to obtain approximately equivalent product distribution is reduced by 6¼ hours (i.e., by about 75 percent or about a 3-fold decrease) by the addition of bromine to the photochlorination process.

EXAMPLE V

Photo-Chlorination of p-Toluenesulfonyl chloride in the Presence of Bromine and Using p-Chloro-α,α,α-trichlorotoluene as the Solvent A one-liter chlorination reactor is fitted with a water cooled light well, a gas sparge tube, thermometer and a condenser which is vented to a sodium bisulfite scrubber. A 100 watt UV (8A3611900) bulb is used as the source of ultraviolet radiation.

A 381.0 g (2 moles) portion of p-chloro-toluenesulfonyl chloride and 300 ml (447 g) of p-chloro-α,α,α-trichlorotoluene are charged to the reactor. The UV light is turned on and chlorine is fed to the process as rapidly as the reaction rate and equipment permits. The initial temperature is 25° C. The theoretical amount of chlorine (426 g) is fed in 3 hours and 8 minutes. GLC analysis at that time indicates that the reaction is about 65 percent complete.

Ten ml of Br$_2$ is then added and the chlorine flow (an additional 260 g) is continued for an additional hour and 32 minutes. The final temperature is 85° C. GLC analysis indicates that the chlorination is now essentially complete (i.e., the reaction mixture is 98+ percent p-chloro-α,α,α-trichlorotoluene). A total of 453 g (900 g recovered minus 447 g solvent) of product is produced, representing a combined product yield of about 98 percent.

EXAMPLE VI

Photochlorination of p-Cresol in the Presence of Bromine

To the apparatus of Example V is charged 200 ml of $CCl_4$ and 325 g (3 moles) of p-cresol. Then 0.5 ml of $Br_2$ is added. The 100 watt UV light is turned on and chlorine is fed to the process at maximum possible rate. The initial temperature is 23° C. Air cooling is used on the light well and the reaction temperature rises to a final temperature of 85° C.

An additional 5 ml portion of $Br_2$ is added after the first two hours of operation and the reaction is continued for 3 hours 52 minutes (5 hours 52 minutes total reaction time). GLC and NMR analyses indicate that the final product is 96+ percent α,α,α-trichloro-p-cresol.

After removing the $CCl_4$ on a roto vacuum, 630 g of product (97.5 percent yield) is recovered.

EXAMPLE VII

Photochlorination of p-Toluenesulfonyl chloride in the Presence of Bromoform

To the reaction vessel of Example V is charged:

| | |
|---|---|
| p-CH₃φSO₂Cl | 191 g (1 M) |
| CCl₄ | 300 g |
| CHBr₃ | 10 g |

The sunlamp is turned on the vessel and chlorine is fed to the reaction vessel slowly until the reaction is initiated. Then the chlorine is fed, with stirring, as rapidly as it can be used. The chlorine feed rate is thus about 120 g/hr for the first 2 hours and about 30 g/hr for the last 3 hours, representing a chlorine charge of about 330 g.

The temperature is controlled between 75° and 85° C by $CCl_4$ reflux. Bromine is released slowly and continually throughout the run. No further additions of $CHBr_3$ are necessary. The reaction proceeds rapidly and is complete at the end of 5 hours.

The product distribution obtained (as determined by GLC analysis) as a function of reaction time is summarized below.

| Chloro-Substituted Product | Reaction Time | | |
|---|---|---|---|
| | 1½ hrs | 3 hrs | 5 hrs |
| p-ClφCH₂Cl | 10% | — | — |
| p-ClφCHCl₂ | 57% | 27% | — |
| p-ClφCCl₃ | 33% | 73% | 97–98% |

After stripping off the $CCl_4$ under vacuum, a 227 g portion (yield) of crude product is recovered. This material is 97+ percent p-ClφCCl₃ (GLC).

While the invention has been described with reference to particular embodiments, it should be understood that such embodiments are not intended to limit the scope of the instantly claimed invention.

What is claimed is:

1. A process for the photochlorination of a methyl aromatic reactant to form an α-chloro-substituted aromatic product, in which process each benzylic hydrogen of the reactant is replaced by a chlorine atom, comprising contacting said reactant with chlorine in the presence of ultraviolet radiation and an accelerating amount of bromine.

2. A process of claim 1 wherein the bromine is provided by elemental bromine or by a brominated organic or inorganic compound which releases bromine under photochlorination conditions.

3. A process of claim 1 wherein the bromine is provided by the methyl aromatic reactant.

4. A process of claim 1 wherein the bromine is provided by elemental bromine.

5. A process of claim 1 wherein the bromine concentration is between about 0.03 and about 3.0 equivalents of bromine atoms per mole of methyl aromatic reactant.

6. A process of claim 1 conducted at a temperature between about 0° and about 200° C.

7. A process of claim 1 conducted in a solvent.

8. A process of claim 7 wherein the bromine is provided by the solvent.

9. A process of claim 7 wherein the solvent is a α-chloro-substituted methyl aromatic product.

10. A process of claim 1 wherein the methyl aromatic reactant has the formula

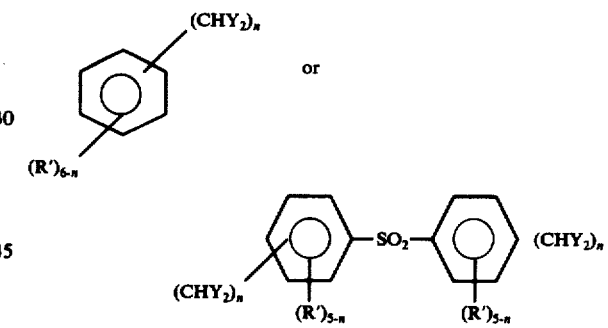

wherein each n is individually a positive integer; each Y is individually hydrogen, chlorine or bromine; and each R' is individually an inert substituent or a chlorine displaceable substituent.

11. A process of claim 10 wherein each n is individually a positive integer of from 1 to 3.

12. A process of claim 10 wherein each n is 1.

13. A process of claim 10 wherein each Y is individually hydrogen or chlorine.

14. A process of claim 10 conducted in a solvent under reflux conditions.

15. A process of claim 10 wherein
  a. the methyl aromatic reactant is p-toluenesulfonyl chloride;
  b. the bromine is provided by elemental bromine, initially present in an amount of about 6.25 mole percent based upon the moles of p-toluenesulfonyl chloride initially charged and supplemented by 2 additions of about 3.12 mole percent each during the course of the photochlorination, based upon the p-toluenesulfonyl chloride initially charged; and
  c. the photochlorination is conducted
    1. in carbon tetrachloride as a solvent comprising about 60 percent by weight of the reaction mixture,
    2. under reflux conditions, and
    3. at a temperature of between about 75° and about 80° C.

* * * * *